US012778660B2

(12) United States Patent
Przygoda et al.

(10) Patent No.: US 12,778,660 B2
(45) Date of Patent: Nov. 3, 2026

(54) SYSTEMS, HUBS, AND CONNECTOR ASSEMBLIES FOR VENOUS DISEASE TREATMENT

(71) Applicant: Venclose, Inc., Franklin Lakes, NJ (US)

(72) Inventors: Darius Przygoda, Mountain View, CA (US); Michael Mirizzi, San Jose, CA (US)

(73) Assignee: Venclose, Inc., Franklin Lakes, NJ (US)

( * ) Notice: Subject to any disclaimer, the term of this patent is extended or adjusted under 35 U.S.C. 154(b) by 224 days.

(21) Appl. No.: 18/696,404

(22) PCT Filed: Oct. 28, 2022

(86) PCT No.: PCT/US2022/078856
§ 371 (c)(1),
(2) Date: Mar. 28, 2024

(87) PCT Pub. No.: WO2023/077054
PCT Pub. Date: May 4, 2023

(65) Prior Publication Data

US 2025/0000565 A1 Jan. 2, 2025

Related U.S. Application Data

(60) Provisional application No. 63/273,769, filed on Oct. 29, 2021.

(51) Int. Cl.
*A61B 18/08* (2006.01)
*A61B 17/00* (2006.01)
*A61B 18/00* (2006.01)

(52) U.S. Cl.
CPC .... *A61B 18/08* (2013.01); *A61B 2017/00199* (2013.01); *A61B 2018/00178* (2013.01); *A61B 2018/00821* (2013.01)

(58) Field of Classification Search
CPC .................. A61B 18/08; A61B 18/082; A61B 18/1206; A61B 18/1492; A61B 2018/00178;
(Continued)

(56) References Cited

U.S. PATENT DOCUMENTS

2004/0172015 A1* 9/2004 Novak .................. A61B 18/12 606/34
2011/0028969 A1 2/2011 Sartor
(Continued)

FOREIGN PATENT DOCUMENTS

WO 2021216959 A1 10/2021

OTHER PUBLICATIONS

International Search Report and Written Opinion dated Feb. 17, 2023, in International Application No. PCT/US2022/078856.

*Primary Examiner* — Khadijeh A Vahdat
(74) *Attorney, Agent, or Firm* — DINSMORE & SHOHL LLP

(57) ABSTRACT

Certain aspects of the present disclosure provide techniques for treating the vasculature of a subject. An energy delivery system includes an energy delivery console, a catheter assembly, and a hub disposed within or attached to the catheter cable assembly. The catheter assembly connects to and receives energy from the energy delivery console. The catheter assembly includes first, second, and third heating elements being serially connected with a first number of connections to supply the energy to different configurations of the first, second, and third heating elements. The hub includes a pair of polarity reversing diodes configured to drive the first, second, and third heating elements of the catheter cable assembly with a second number of connections disposed between the energy delivery console and the catheter cable assembly. The second number of connections is one less than the first number of connections.

17 Claims, 10 Drawing Sheets

(58) Field of Classification Search

CPC ........... A61B 2018/00404; A61B 2018/00577; A61B 2018/00821; A61B 2018/124; A61B 2018/1246; A61B 2018/1286; A61B 2018/1467; A61B 2017/00199; A61B 90/90; A61B 2090/0813

See application file for complete search history.

(56) References Cited

U.S. PATENT DOCUMENTS

| | | | | |
|---|---|---|---|---|
| 2013/0196721 | A1* | 8/2013 | Waterman .............. | H04R 1/105 455/575.2 |
| 2014/0276798 | A1 | 9/2014 | Batchelor et al. | |
| 2015/0272654 | A1* | 10/2015 | Esch .................. | A61B 18/1492 606/34 |
| 2019/0014410 | A1* | 1/2019 | Krishnamoorthy .... | H04R 3/007 |
| 2021/0204997 | A1 | 7/2021 | Frushour | |
| 2021/0330370 | A1 | 10/2021 | Macaraeg et al. | |

* cited by examiner

SYSTEMS, HUBS, AND CONNECTOR ASSEMBLIES FOR VENOUS DISEASE TREATMENT

CROSS-REFERENCE TO RELATED APPLICATIONS

This application is a U.S. National Phase of International Application No. PCT/US2022/078856, entitled "Systems, Hubs, And Connector Assemblies For Venous Disease Treatment" filed Oct. 28, 2022, which claims the benefit of U.S. Provisional Patent Application No. 63/273,769, filed Oct. 29, 2021, entitled "METHODS AND SYSTEMS FOR VENOUS DISEASE TREATMENT," which are each incorporated by reference in [its] their entirety.

FIELD

The present disclosure is directed to systems, hubs, and connector assemblies for vascular treatment, and particularly to systems, hubs, and connector assemblies for treating incompetent veins of a subject.

BACKGROUND

Blood vessels and other physiological structures can fail to perform their proper function. An example, in the case where opposing valve leaflets within a vein do not touch each other, blood flow within the vein is not predominately restricted to one direction towards the heart. This condition is called venous reflux, and it causes elevated localized blood pressure within the vein. Elevated localized blood pressure is subsequently transferred to the surrounding tissue and skin. Furthermore, failure of a valve in a vein causes a cascading reaction of successive failure of valves along the vein. In order to standardize the reporting and treatment of the diverse manifestations of chronic venous disorders, a comprehensive clinical-etiology-anatomy-pathophysiology (CEAP) classification system has been developed to allow uniform diagnosis. The CEAP classification is commonly used to describe the level of subject symptoms, which increase in severity from spider veins, to varicose veins, to swelling (edema), to skin changes (bluish staining, lipodermatosclerosis), to previously healed ulcer, finally to active ulceration which is regarded most severely. Chronic venous insufficiency is a term often used to describe the more severe symptoms of chronic peripheral venous disease.

The human lower extremity veins consist of three systems: the superficial venous system, the deep venous system, and the perforating venous system, which connects the superficial and the deep systems. The superficial system includes the great saphenous vein (GSV) and the small saphenous vein (SSV), among others. The deep venous system includes the anterior and posterior tibial veins, which unite to form the popliteal vein that in turn becomes the femoral vein when joined by the small saphenous vein.

Perforator veins connect the deep venous system of a leg to the surface veins which lie closer to the skin. Normal or healthy perforator veins pass blood from the surface veins to the deep veins as part of the normal blood circulation. Incompetent perforator veins allow blood flow from the deep venous system to the surface veins, causing or contributing to problems, such as varicose veins, edema, skin and soft tissue changes, lipodermatosclerosis, chronic cellulites, venous ulcers, and the like.

Several procedures have been proposed for interruption of incompetent perforator veins. The "Linton" procedure requires a very long incision (knee to ankle) on the medial calf to expose the perforator veins. Individual veins may then be surgically dissected, ligated, and cut to prevent blood flow between the superficial and deep venous systems. A less invasive alternative has been developed by DePalma where individual incompetent perforator veins are identified along "Linton's Line" using ultrasound. Small incisions are then used to access the individual perforators for ligation and dissection. More recently, individual ligation and dissection of perforator veins has been performed using an endoscope inserted in the proximal calf.

Although generally effective, each of the above-described procedures requires surgical incisions followed by ligation and cutting of the veins. Thus, even at best, the procedures are traumatic to the subject and require significant surgical time. Moreover, the procedures are complex and often require a second surgeon to assist in the procedure.

SUMMARY

Embodiments of the present disclosure address the above-noted deficiencies of convention procedures by providing simplified, less invasive procedures for ablating veins having incompetent valves.

In one embodiment, an energy delivery system includes an energy delivery console, a heated catheter, and a hub disposed within or attached to the heated catheter. The heated catheter connects to and receives energy from the energy delivery console. The heated catheter includes first, second, and third heating elements being serially connected with a first number of connections to supply the energy to different configurations of the first, second, and third heating elements. The hub includes a pair of polarity reversing diodes configured to drive the first, second, and third heating elements of the catheter cable assembly with a second number of connections disposed between the energy delivery console and the heated catheter. The second number of connections is one less than the first number of connections.

In another embodiment, a hub interfaces between a heated catheter and an energy delivery console. The hub includes a tip, ring, and sleeve (TRS) connector jack configured to provide a number of terminals to a corresponding TRS connector plug of the energy delivery console. The hub also includes a pair of polarity reversing diodes connected to one of the terminal. The hub drives first, second, and third heating elements of the heated catheter with a number of connection points, the number of connection points being one more than the number of terminals.

In yet another embodiment, a connector assembly electrically couples a heating catheter having a short heating element and a long heating element to an energy delivery console. The connector assembly includes a first connector jack configured to provide a first input electrical connection and a second input electrical connection to provide power for the heating catheter. The connector assembly also includes a pair of polarity reversing diodes electrically coupled to the first input electrical connection. The pair of polarity reversing diodes electrically coupling the first input electrical connection to a first heating element connection and a second heating element connection, the second input electrical connection being electrically coupled to a third heating element connection. Additionally, the connector assembly includes a second connector jack configured to pass through communication signals between the heating catheter and the energy delivery console.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

In general, various aspects and embodiments of the present invention relate to medical methods and apparatus for heat treatment catheters that, when coupled to a compatible generator via for example, a single-TRS connector or dual-TRS connector, are suited for use in heat treatment of vascular structures. Technologies for treating varicose veins, such as may result from venous valve insufficiency, using RF ablation typically have two components: a power source (i.e., the generator) and a thermal ablation delivery device (i.e., the catheter). The catheter is typically a single subject use disposable device that is used during the procedure and then discarded. Manufacturers of these technologies often build thousands of these disposable catheters per month. There is typically a significant amount of cost built into the catheter in the form of sophisticated electronics. The catheter electronics are expensive and are also exposed to procedure hazards which can lead to product quality issues in the field. However, there are challenges to simplifying the disposable catheters. For example, different configurations of heating catheters have different connections to drive the heating coils.

As described herein electronic components to drive the heating coils of the heated catheters are placed within an energy delivery system. However, different heated catheters may have different configurations. For example, some heated catheters may have one, two, three or more heating coils. Additionally, because heated catheters are typically one-use items, it is desirable to limit the number of connections (e.g., wires, etc.) between the heated catheter and the energy delivery system and thus reduce the materials used to construct the heated catheter. Additionally, as the capability of the heated catheter changes over time (e.g., number of heating coils, number of memory circuits/chips, etc.), it is desirable to provide a system to facilitate using the same electronics of the energy delivery system even as the configuration of the heated catheters change. As described herein, a hub is configured to facilitate the connection between the energy delivery system and the heating coils of the heated catheters. The hub reduces the number of connections between the hub and the energy delivery system to drive the heated coils of the heated catheters in different configurations. For example, a heated catheter may have two heating coils that can be driven singly or in combination with three electrical connections. In such an example, the hub may provide two electrical connections to the energy delivery system to drive the heating coils singly or in combination. Additionally, the hub provides a standardized connector configuration that inhibits the hub from being incorrectly inserted into the energy delivery system and provides a connection configuration that may be used across different heated catheters with different capabilities.

Figure 1:
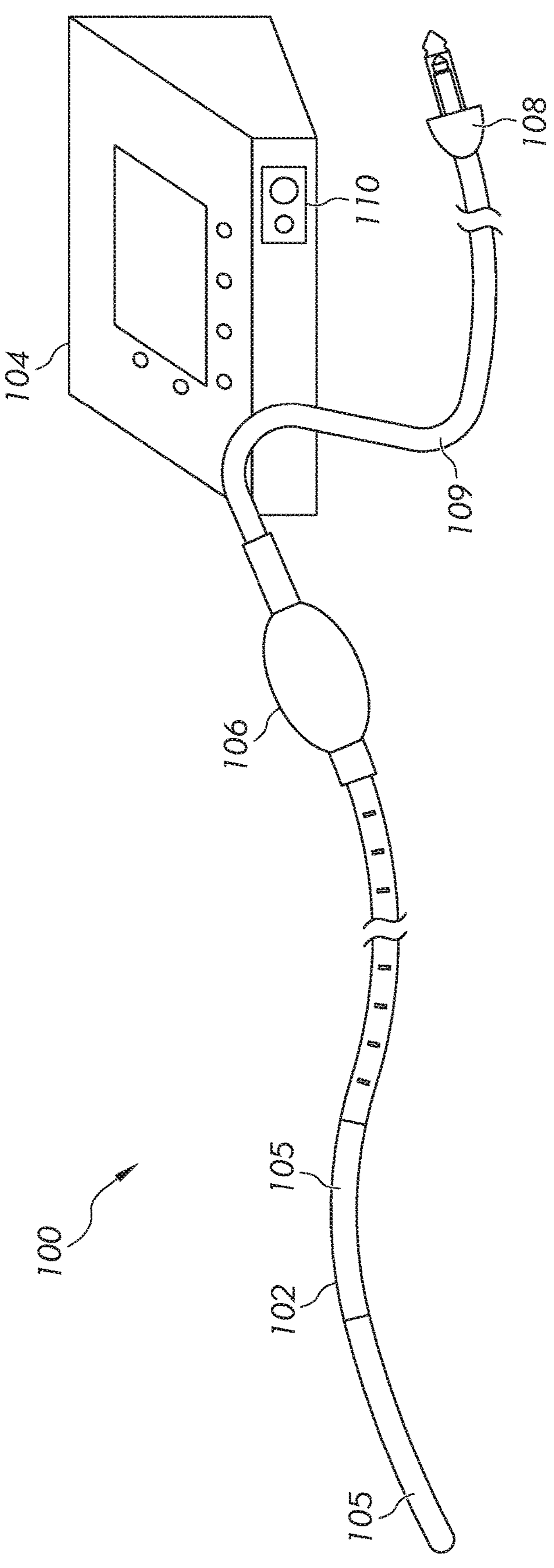
FIG. 1 schematically illustrates an example of an energy delivery system for providing endovenous thermal ablation, according to one or more embodiments shown and described herein.

FIG. 1 depicts an energy delivery system 100 for performing thermal ablation. In this example, the energy delivery system 100 includes a heated catheter 102, and an energy delivery console 104. In the illustrated example, the heated catheter 102 is a long, thin, flexible, or rigid device that can be inserted into a narrow anatomical lumen such as a vein. Examples of systems and methods to use a heated catheter 102 to treat venous disease are described in International Application No. PCT/US2021/028779, entitled "METHODS AND SYSTEMS FOR VENOUS DISEASE TREATMENT," incorporated by reference in its entirety. The heated catheter 102 is connected to energy delivery console 104 to provide energy to drive one or more heating elements 105 that heat the distal end of the heated catheter 102, which can be placed within the lumen of a vein to be treated. As an example of treating venous disease, the heated catheter 102 can be inserted into a target region of a perforator vein at or below a facia layer. The heating element(s) 105 of the heated catheter 102 can be activated to provide heat therapy or heat treatment to the target region at or below the fascia layer. More than one treatment cycle can be performed in the same position within the vein before moving to the next treatment site. The heated catheter 102 can be moved (e.g., withdrawn proximally towards the entry point through the skin of the patient) to a second target region within, for example, the perforator vein, but still at or below the fascia layer. More heat treatments can be applied at subsequent target regions. These subsequent regions can be treated with all of the heating elements 105 or a subset of the heating elements as described herein. The heated catheter 102 can be moved (e.g., retracted) to a third target region of the PV, this time above the fascia layer. Additionally, the heating element(s) 105 can be activated to provide heat therapy to the third target region above the fascia layer.

The heating elements 105 have an associated resistance causing them to heat up when electrical current passes through them enabling heat energy to be produced that is eventually applied to the vein wall by conduction (conductive heating). The heating elements 105 generate heat regardless of the direction of current flowing through them. In some examples, the energy delivery console 104 provides energy to drive one or more heating elements 105 to heat the heated catheter 102 at varying lengths along the distal end of heated catheter 102. In some examples, to power and control both longer-length and shorter-length heating elements 105, the energy delivery console 104 adjusts the power source voltage based on the lengths of the heating elements 105 to be energized. In some examples, the heating elements 105 have resistances to achieve approximately 5.7 W/cm of maximum heating, which is then reduced to lower levels of heating as necessary to maintain a target temperature. This level of heating is an appropriate match for a studied protocol for thermal ablation of veins at 120° C. with a reasonably fast heating time, but alternative perturbations of higher or lower maximum heating may also be employed; examples are greater than 6 W/cm for even faster heating or to a higher temperature, or over a larger diameter heating element, or less than 5 W/cm for slower heating or to a lower temperature.

In the illustrated example, the heated catheter 102 includes a hub 106 and a connector 108. The hub 106 includes electronics that provide catheter data (e.g., memory storing a catheter identifier (ID) and catheter usage data, a temperature sensor, etc.), connections configured for the heating elements 105 of the heated catheter 102, and/or connections to a thermocouple, etc. The connector 108 provides an electrical connection between the energy delivery console 104 and the hub 106. The connector 108 plugs into corresponding plugs 110 of the energy delivery console 104. The connector 108 is configured to plug into the energy delivery console 104 in a manner that inhibits incorrectly inserting the connector 108. In the illustrated example, the connector 108 includes two jacks of different physical configurations (e.g., a jack with a first length and diameter, and a jack with a second length and diameter, etc.). In the illustrated example, the connector 108 is electrically coupled to the hub 106 via a wire harness 109. While the connector 108 illustrated in FIG. 1 to interface with the energy delivery console 104 includes two jacks, the energy delivery console 104 may be configured to be compatible with heated catheters that include only one jack such that the energy delivery console 104 is backwards compatible with older heated catheters.

Figure 2:
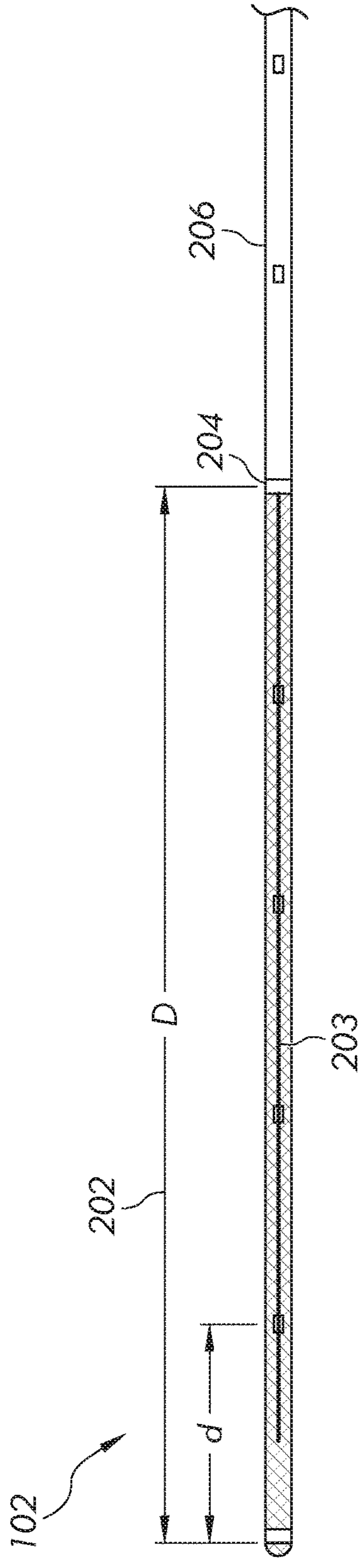
FIG. 2 schematically illustrates a heating element of a heating catheter for providing endovenous thermal ablation, such as with the energy delivery system of FIG. 1, according to one or more embodiments shown and described herein.

FIG. 2 depicts the heated catheter 102 having a catheter tube 202 including one or more of the heating elements 105. The heating element is heated by electrical current flowing through one or more heating elements 105. In some examples, the heated catheter 102 includes multiple heating elements 105 connected in series. In some such examples, the active heating length of catheter tube 202 is configured to be selectable by the user by directing electrical current to one or more of the heating coils. For example, the active heating length may be selectable from 1 cm to 10 cm. In such an example, a user (e.g., doctor, surgeon, etc.) may select a heating length as small as d (e.g., 1 cm) that corresponds to a first heating coil up to a length of D (e.g., 10 cm) that corresponds to the first heating coil and a second heating coil, for example, by selecting a switch on heated catheter 102 or energy delivery console 104. In such an example, when the small length d is selected, electrical current is directed through the first heating coil and when the long length D is selected, electrical current is directed through the first and second heating coils.

The heated catheter 102 includes a temperature sensor 203 (e.g., thermocouple or thermistor) located along the length of the heating coil(s) 105, such as at a position 1-3 cm from the distal end of heated catheter 102. The temperature sensor may be placed between coil winds (with spacing or insulation to prevent electrical shorting across coils), over the coil assembly (insulated, for example, by a layer over the metal coil such as FEP, PTFE or parylene to prevent electrical shorting across coils), under the coil assembly, or within the body of heated catheter 102 under the heating element area.

In the illustrated example, markings 204 and 206 may be provided at different lengths along heated catheter 102 to guide a user by visual cues/. The markings 206 may be in the form of a series of dots, spaced approximately equal to the length of the shortest heating length d. The markings 204 may provide another visual cue, and may be in the form of a series of lines, spaced approximately equal to the length of the longer heating length D. The markings 204 and 206 mark where the shorter length of heating is and/or facilitate segmental positioning and heating of the shorter length of heating within the blood vessel. In some examples, the markings 204 and 206 are geometric lines or shapes, alphanumeric characters, color-coded features, or a combination thereof. In some examples, the markings 204 and 206 are placed at intervals approximately equal to the length of the heating element (such as 10 cm apart when the heating element is 10 cm long), or slightly longer than the heating element (such as 10.1 cm apart when the heating element is 10 cm long) to prevent accidental overlapping of treatments. Prevention of overlap of the heating segments has two main advantages: first, avoiding overlaps helps with the speed of the procedure, as the treatments will ablate the longest possible length of vessel with each treatment, and second, overlap of treatments creates additional heating at the overlap region and this may lead to unnecessary tissue injury. The markings 204 and 206 may include alignment markings to facilitate location of the heating element and/or tubing bonds. In a specific implementation, a marking or discernable feature can indicate a minimal distance of treatment away from the active length of the heating element, giving the user a cue to avoid tissue heating too near the subject's skin. In one example, a marking or edge of a tubing layer or bond can be 2.5 or 3.0 cm proximal to the proximal end of the heated catheter 102.

Figure 3:
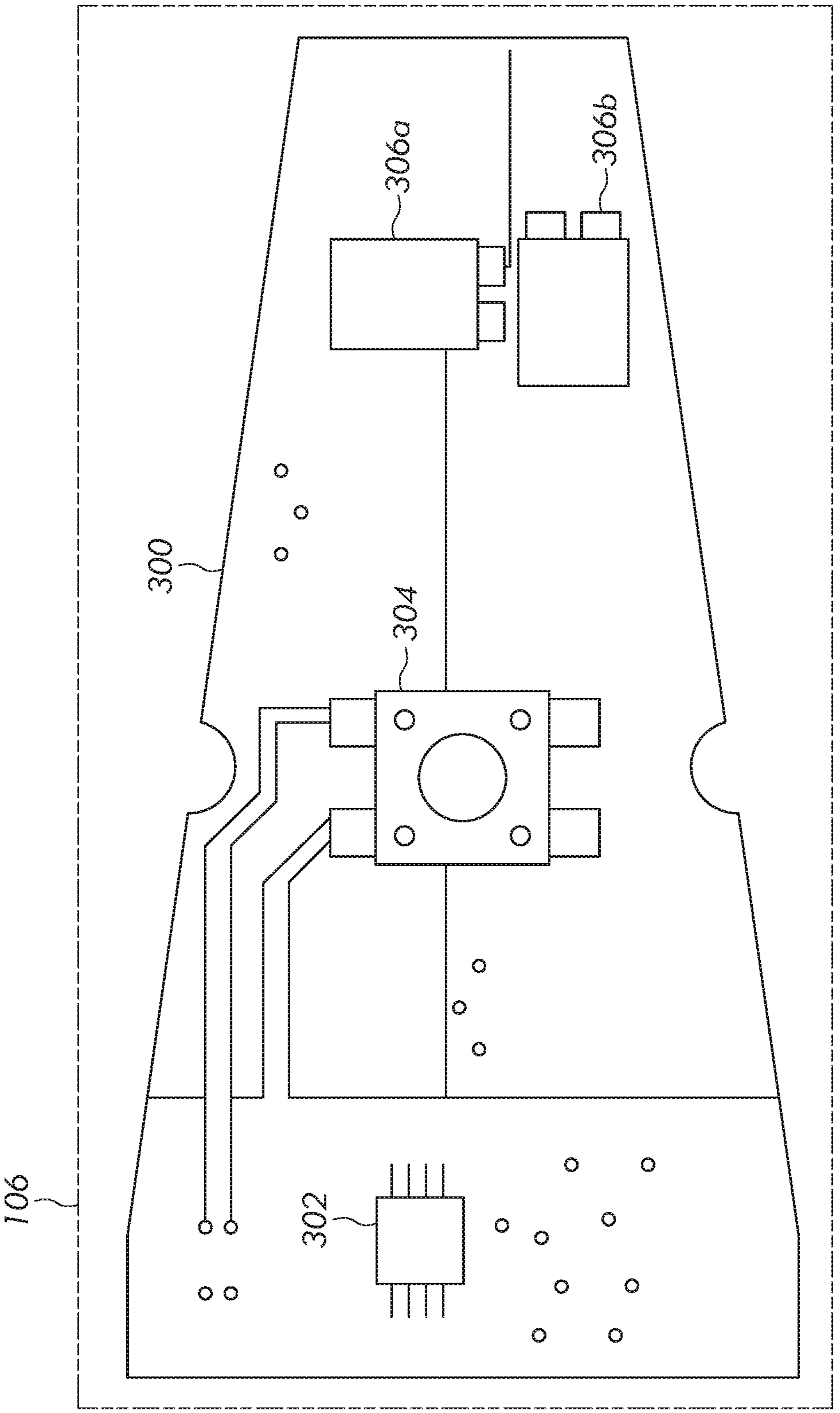
FIG. 3 schematically illustrates an circuit board of a hub to interface between the heating element of the heating catheter of FIG. 2 and the energy delivery system, according to one or more embodiments shown and described herein.

FIG. 3 illustrates an example circuit board 300 of the hub 106 to interface between the catheter tube 202 of the heated catheter 102 and the energy delivery console 104. In the illustrated example, the hub 106 is configured to interface with an energy delivery system (such as, the energy delivery console 104 of FIG. 1) where circuitry to drive the heating elements 105 is located in the re-usable energy delivery console 104. As described here, the simplified and versatile hub 106 reduces the price and complexity of the disposable component (i.e., the heated catheter 102) and also reducing the amount of electronic waste since those components now reside in the reusable component (i.e., the energy delivery console 104).

In the illustrated example, the circuit board 300 includes a hub information component 302, a thermocouple reference switch 304, a pair of polarity reversing diodes 306*a* and 306*b* and connections for the temperature sensor 203 measuring the temperature of the heating coil(s) 105 of the heated catheter 102. A greater or fewer number of components may be included without departing from the scope of the present disclosure.

The hub information component 302 may, for example, be a memory integrated circuit, such as an EEPROM, that stores a unique identifier for the heated catheter 102 and/or data associated with usage of the heated catheter 102 (e.g., date when it was first used, total usage time, etc.). The unique identifier may be used, for example, by the energy delivery console 104 to determine the configuration (e.g., number of coils, which terminals correspond to which of the coils, etc.) of the heated catheter 102 by, for example, comparing the unique identifier to a database for records that associate the unique identifiers to models and/or configuration settings. This database may be stored in the energy delivery console 104 may be store in a cloud storage system accessible by the energy delivery console 104. The energy delivery console 104 then manipulates the power drivers within the energy delivery console 104, as described below, to drive the particular heated catheter 102 according to the arrangement of its heating elements 105 as determined by the configuration.

In some examples, the hub information component 302 is a digital temperature sensor integrated with EEPROM memory. The Seebeck Effect states that an electromotive force develops across two points of electrically conducting materials when there is a temperature difference between the materials (sometimes referred to as a "cold junction"). The difference of temperatures between the distal end of the catheter tube 202 and the hub 106 is converted into electrical voltage. In order to accurately measure the temperature at the distal end of the catheter tube 202, the temperature at the cold junction (sometimes referred to as the "cold reference junction temperature") has to be known in order to correctly calibrate the temperature measurement. The hub information component 302 also provides a thermocouple cold junction reference to overcome the Seebeck Effect to correctly calibrate the temperature measurement of the heated catheter 102 by providing a temperature at the cold junction between the heating elements 105 and the energy delivery console 104.

The terminals of some of the heating elements 105 are electrically coupled to the polarity reversing diodes 306*a* and 306*b*. As described below, the polarity reversing diodes 306*a* and 306*b* connects two heating coil-side terminals to one connector-side terminal and restrict the flow of current such that current can only flow in or out of one of the heating coil-side terminals. By reversing the polarity of the power source on the one connector-side terminal, the energy delivery console 104 determines through which of the two heating coil-side terminals the current flows. The polarity reversing diodes 306*a* and 306*b* optionally allow control of the heating coils using fewer connector-side terminals overall.

In some examples, the circuit board 300 is a multilayer circuit board with the components (e.g., the hub information component 302, the thermocouple reference switch 304, the pair of polarity reversing diodes 306*a* and 306*b*, etc.) are connected using copper traces and vias (e.g., a blind via, a buried via, a through hole via, etc.) between layers. For simplicity, all of the vias and traces are not reproduced in FIG. 3, but may be configured according to the corresponding circuit diagram (e.g., the circuit diagram of FIG. 4 below).

Figure 4:
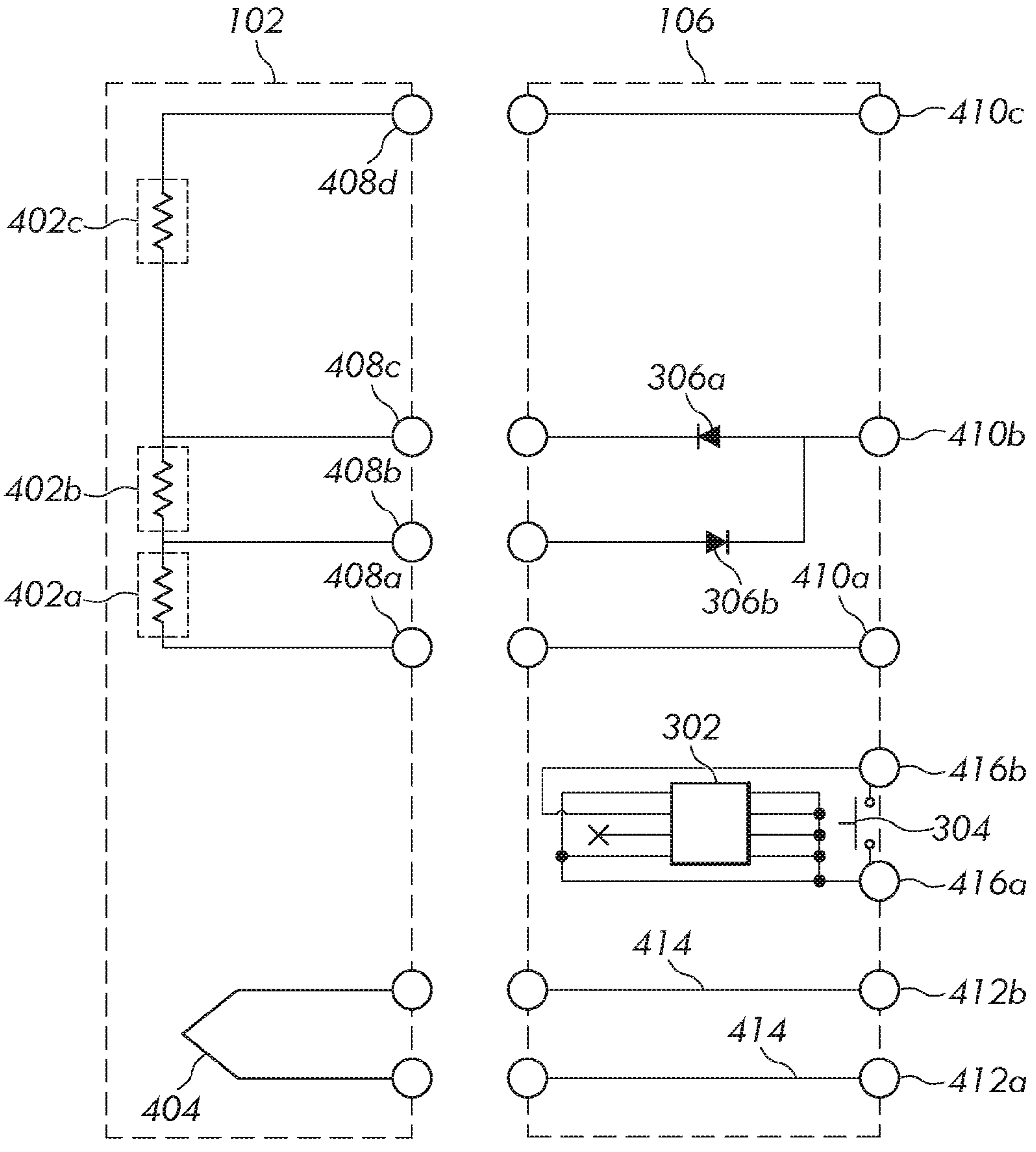
FIG. 4 schematically illustrates catheter heater coil connections to a cable interface through polarity reversing diodes of the hub of FIG. 3, according to one or more embodiments shown and described herein.

FIG. 4 is a circuit diagram 400 that illustrates connections between the heating elements 402*a*, 402*b*, and 402*c* (collectively "heating elements 402") of the heated catheter 102 to the connector 108 through hub 106. The heating elements 402 of FIG. 4 may be an example of the heating elements 105 of FIG. 1. The heating elements 402 may be made of one or more resistive coil segments These coil segments may not be separate components, but may be a single coil component. In the illustrated example, the heating elements 402 and temperature sensor 404 of the heated catheter 102 detachably interface with the hub 106 via a connector (e.g., a high contact density push-pull or break-away connector with high current capacity, etc.). Alternatively, in some examples, the heating elements 402*a*, 402*b*, and 402*c* and temperature sensor 404 may be directly connected to the electronics of the hub 106. The temperature sensor 404 is an example of the temperature sensor 203 of FIG. 2. In the illustrated example, the heated catheter 102 includes three heating coils (e.g., a short heating element 402*a*, a long heating element 402*b*, and an extended heating element 402*c*). For example, the short heating element 402*a* may be 2.5 centimeters (cm) long at the distal end of the heated catheter 102, the long heating element 402*b* may extend to the next 7.5 cm of the heated catheter 102, and the extended heating element 402*c* may extend to the next 10 cm of the heated catheter 102 after the long heating element 402*b*. In such an example, the short heating element 402*a* (2.5 cm long) and the long heating element 402*b* (7.5 cm long) together extend 10 cm from the distal end of the heated catheter 102. In such an example, if the user desires to heat up the first 10 cm of the heated catheter 102, the energy delivery console 104, though the hub 106, directs current through the short heating element 402*a* and the long heating element 402*b*. In some examples, the heated catheter 102 may have more (e.g., four or more) or fewer (e.g., two) heating elements 402.

In the illustrated example, the heating elements 402 are connected serially with the connection points 408*a*, 408*b*, 408*c*, and 408*d* (collectively "connection points 408") at the terminals of the heating elements 402. The connection points 408 are points at which two or more electronic elements are connected and are used herein for illustrative purposes to describe how electronic elements are connected. The connection points 408 may, for example, connect to pins of connectors. For example, two of the connection points 408*a* and 408*b* are at the terminals of the short heating element 402*a*, two of the connection points 408*b* and 408*c* are at the terminals of the long heating element 402*b*, and two of the connection points 408*c* and 408*d* are at the terminals of the extended heating element 402*c*. Generally, there are one more connection points 408 than there are heating elements 402. For example, a heated catheter 102 with two heating elements 402 has three connection points 408, and a heated catheter 102 with three heating elements 402 has four connection points 408.

In the illustrated example, each of the polarity reversing diodes 306*a* and 306*b* of the hub 106 is electrically coupled to a respective one of two of the connection points 408. The connector 108, via the hub 106, has one less heating terminal 410*a*, 410*b*, and 410*c* (collectively "heating terminals 410") than the number of connection points 408. The heating terminals 410 are electrically coupled to one jack of the connector 108 that plugs into the power management circuit of the energy delivery console 104. In the illustrated example, only six conductors are required to power a duel-heating element catheter (e.g., instead of seven) and only seven conductors are required to power a three-heating element catheter (e.g., instead of eight). The polarity reversing diodes 306*a* and 306*b* coupled to two of the connection points 408 to one of the heating terminals 410. Because of the polarity reversing diodes 306*a* and 306*b*, by reversing the direction of electrical current, which of the connection points 408 the electrical current will flow through is selectable (e.g., by the power management circuit of the energy delivery console 104). Activating the heating elements 402 of the circuit diagram 400 is described on Table 1 below when the heated catheter 102 includes the short heating element 402*a*, the long heating element 402*b*, and the extended heating element 402*c*. On Table 1: (i) $T_1$ is the first heating terminal 410*a*, $T_2$ is the second heating terminal 410*b*, and $T_3$ is the third heating terminal 410*a*, (ii) $C_1$ is the first connection point 408*a*, $C_2$ is the second connection point 408*b*, $C_3$ is the third connection point 408*c*, and $C_4$ is the fourth connection point 408*d*, (iii) GND is a connection to ground, PWR is a connection to power, and FLT is a floating connection, and (iv) $H_S$ is short heating element 402*a*, $H_L$ is long heating element 402*b*, and $H_E$ is extended heating element 402*c*.

TABLE 1

| Terminal | | | Current | | Heater(s) Activated | | |
|---|---|---|---|---|---|---|---|
| PWR | GND | FLT | From | To | $H_S$ | $H_L$ | $H_E$ |
| $T_1$ | $T_2$ | $T_3$ | $C_1$ | $C_2$ | Yes | No | No |
| $T_2$ | $T_1$ | $T_3$ | $C_3$ | $C_1$ | Yes | Yes | No |
| $T_1$ | $T_3$ | $T_2$ | $C_1$ | $C_4$ | Yes | Yes | Yes |
| $T_2$ | $T_3$ | $T_1$ | $C_3$ | $C_4$ | No | No | Yes |
| $T_3$ | $T_2$ | $T_1$ | $C_4$ | $C_2$ | No | Yes | Yes |

When the user selects which length of the heated catheter 102 to be heated, the power management circuit of the energy delivery console 104 connects power and ground to the corresponding heating terminals 410.

Activating the heating elements 402 of the circuit diagram 400 is described on Table 2 below when the heated catheter 102 includes the short heating element 402*a* and the long heating element 402*b*. On Table 2: (i) $T_1$ is the first heating terminal 410*a* and $T_2$ is the second heating terminal 410*b*, (ii) $C_1$ is the first connection point 408*a*, $C_2$ is the second connection point 408*b*, and $C_3$ is the third connection point 408*c*, (iii) GND is a connection to ground and PWR is a connection to power, and (iv) $H_S$ is short heating element 402*a* and $H_L$ is long heating element 402*b*.

TABLE 2

| Terminal | | Current | | Heater(s) Activated | |
|---|---|---|---|---|---|
| PWR | GND | From | To | $H_S$ | $H_L$ |
| $T_1$ | $T_2$ | $C_1$ | $C_2$ | Yes | No |
| $T_2$ | $T_1$ | $C_3$ | $C_1$ | Yes | Yes |

In the illustrated example, the hub 106 includes pass through traces 414 that connect to temperature sensor terminals 412*a* and 412*b* (collectively the "temperature sensor terminals 412") of the connector 108 to electrically couple the temperature sensor 404 of the heated catheter 102. The hub information component 302 is connected to the data terminals 416*a* and 416*b* (collectively the "data terminals 416") of the connector 108. In the illustrated example, the hub information component 302 is powered and communicates with the generator via 1-wire communication link to minimize the number of connections to two (e.g., a signal connecter at data terminal 416*a* and ground connection at data terminal 416*b*). To further minimize the number of connections between the hub 106 and the energy delivery console 104, the 1-wire link is shared with the thermocouple reference switch 304. The thermocouple reference switch 304 is connected between the data terminals 416*a* and 416*b*. A power switch driver located in the generator enables the dual-TRS connector described above and also maintains backwards compatibility with catheters that use a legacy 6.35 mm single-TRS connector.

Figure 5A:
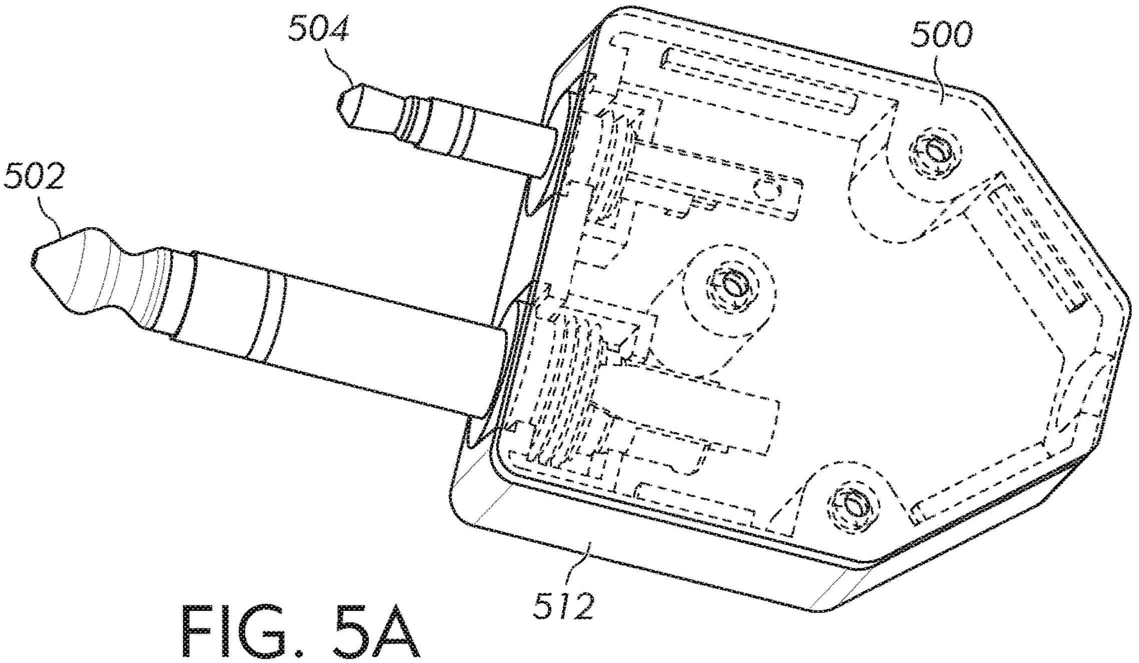
FIG. 5A schematically illustrates a dual-jack connector configured to couple a heating catheter to an energy delivery system, according to one or more embodiments shown and described herein.
Figure 5B:
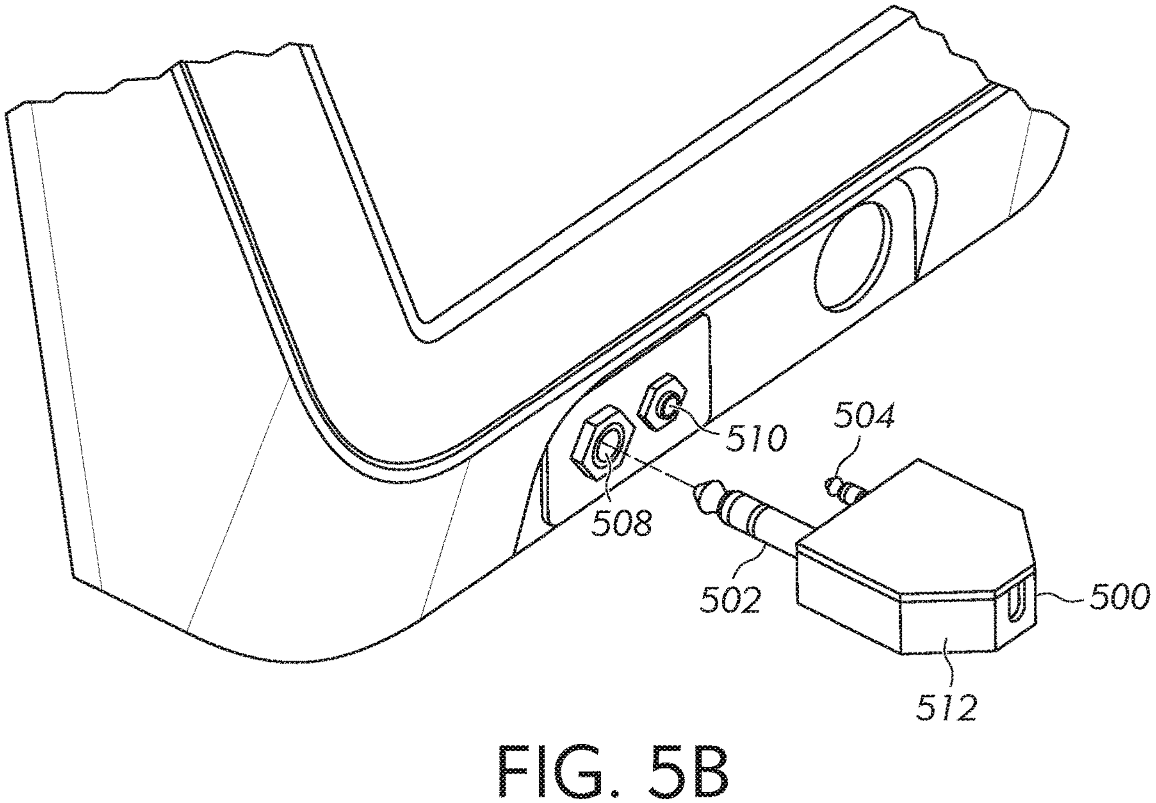
FIG. 5B schematically illustrates the dual-jack connector of FIG. 5A aligned to couple with an energy delivery system, according to one or more embodiments shown and described herein.

FIGS. 5A and 5B illustrate an example connector 500 configured to couple the heated catheter 102 to the energy delivery console 104. The connector 500 of FIGS. 5A and 5B is an example of the connector 108 of FIG. 1. As illustrated in FIG. 5A, the connector 500 includes a first Tip, Ring, and Sleeve (TRS) jack 502 and a second TRS jack 504. The first and second TRS jacks 502 and 504 have different physical characteristics to promote the connector 500 being pluggable into the energy delivery console 104 with a single orientation. This optionally helps to avoid incorrect connection of the connector to the energy delivery console. In the illustrated example, the first TRS jack 502 is a 6.35 mm TRS jack configured for higher current conductors and the second TRS jack 504 is a smaller 3.5 mm TRS jack configured to carry low current signals between the heated catheter 102 and the energy delivery console 104. FIG. 5B illustrates the connector 500 interfacing with the energy delivery console 104. The energy delivery console 104 includes plugs 508 and 510 configured to receive the first and second TRS jack 502 and 504. The plugs 508 and 510 are an example of the plugs 110 of FIG. 1.

In the illustrated examples, the connector 500 includes a shell 512 configured to receive a wire harness to connect the first and second TRS jacks 502 and 504 to the terminals 410, 412, and 416 of the hub 106. In some examples, the connector 500 may be incorporated into a housing of the hub 106 and connect the terminals 410, 412, and 416 to the first and second TRS jacks 502 and 504 via wiring inside the housing of the hub 106.

Figure 6:
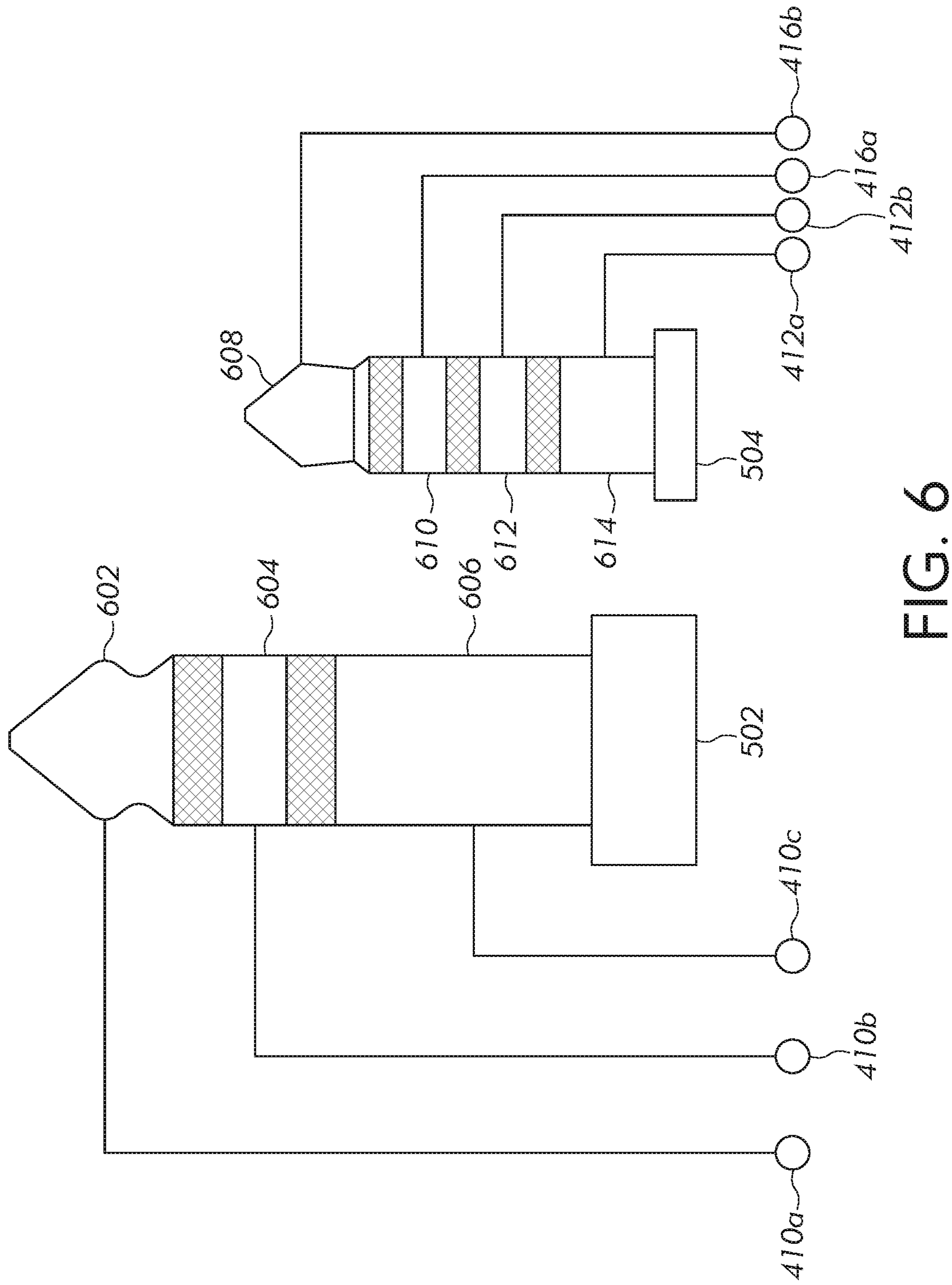
FIG. 6 schematically depicts a wiring of a dual-jack connector to a hub of a heating catheter, according to one or more embodiments shown and described herein.

FIG. 6 illustrates conceptual connections between the terminals 410, 412, and 416 of the hub 106 and the first and second TRS jacks 502 and 504. The connections illustrated in FIG. 6 are example connections. In the illustrated example, the first TRS jack 502 includes a tip 602, a ring 604, and a sleeve 606. The first TRS jack 502 has higher current conductors to transmit electrical current sufficient to heat the heating elements 402. In the illustrated example, the second TRS jack 504 includes a tip 608, a first ring 610, a second ring 612, and a sleeve 614 (sometimes referred to as a "TRRS jack"). The second TRS jack 504 is configured to carry low current signals. While the second TRS jack 504 includes two rings 610 and 612 to provide a total of four connection points, the second TRS jack 504 may have more or fewer rings. For example, the hub information component 302 may have a 2-wire communication bus or the heated catheter 102 may only have two heating elements 402.

In the illustrated example, the tip 602 of the first TRS jack 502 is electrically coupled to the first heating terminal 410*a*, the ring 604 of the first TRS jack 502 is electrically coupled to second heating terminal 410*b*, and the sleeve 606 of the first TRS jack 502 is electrically coupled to the third heating terminal 410*a*. In some examples, when the heated catheter 102 has less than three heating elements 402, the one or more of the tip 602, a ring 604, and a sleeve 606 may not be electrically coupled to any connection point 408. In the illustrated example, the tip 608 and the first ring 610 of the second TRS jack 504 are electrically coupled to the data terminals 416, and a second ring 612 and the sleeve 614 of the second TRS jack 504 are electrically connected to the temperature sensor terminals 412. Different configurations of heated catheter 102 may have different connections to the TRS jacks 502 and 504, where the first TRS jack 502 is connected to the heating terminals 410 in any configuration and the temperature sensor terminals 412 and the data terminals 416 are connected to the second TRS jack 504 in any configuration. The energy delivery console 104 may determine how to switch power and ground to the first TRS jack 502 based on the identity associated with the heated catheter 102.

Figure 7:
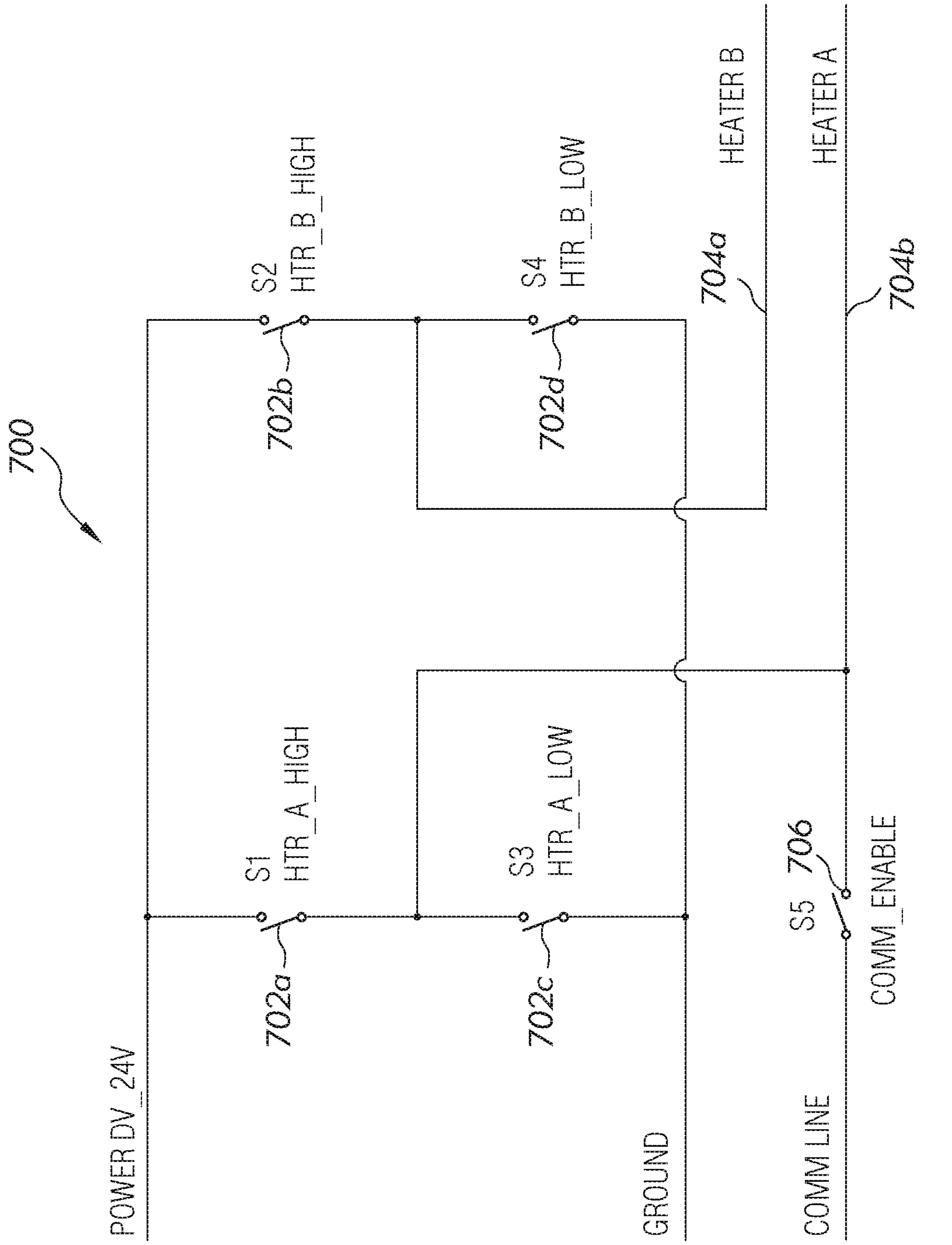
FIG. 7 schematically illustrates a power switch diagram configured to deliver different configurations of power to the two heating elements of the heated catheter through the hub, according to one or more embodiments shown and described herein.

FIG. 7 illustrates an example connection diagram of a power switch circuit 700 of the energy delivery console 104 configured to deliver different configurations of power to the heating elements 402 of the heated catheter 102 through connector 108 and the hub 106. The power switch circuit 700 applies voltage to energize the heating elements 402 and applies voltage and ground to different terminals of the first TRS jack 502 depending on the heated catheter 102 that is used and which of the heating elements 402 is to be energized. The power switch circuit 700 of FIG. 7 switches the power and ground connections to different terminals of the first TRS jack 502 depending on the identity of the heating catheter plugged in and/or the heating coil(s) 402 that the user desires to be energized. In the illustrated example, the power switch circuit 700 supports heating catheters with one or two heating elements 402. The power switch circuit 700 includes switches 702*a*, 702*b*, 702*c*, and 702*d* (e.g., solid-state relays, etc.). In the illustrated example, the switches are configured in an H-bridge circuit configuration. The switches 702*a*, 702*b*, 702*c*, and 702*d* implement a change of polarity on lines 704*a* and 704*b* connected to the terminals of the plug 110 that corresponds to the first TRS jack 502. For some heating catheters that only use the first TRS jack 502, the line 704*b* becomes a communication signal line. If the first high switch 702*a* and the second low switch 702*d* are closed and the second high switch 702*b* and the first low switch 702*c* are open, one line 704*a* is connected to POWER and the other line 704*b* is connected to ground (GND). If the second high switch 702*b* and the first low switch 702*c* are closed and the first high switch 702*a* and the second low switch 702*d* are open, one line 704*a* is connected to GND and the other line 704*b* is connected to ground POWER. In addition, a communication enable switch 706 may be closed when the first high switch 702*a* and the second low switch 702*d* are open to allow for a communication signal for heated catheter 102 using just the first TRS jack 502. The communication enable switch 706 may be included to, for example, provide backwards compatibility with older heated catheter models that only use a single jack for both power deliver and data communication.

Figure 8A:
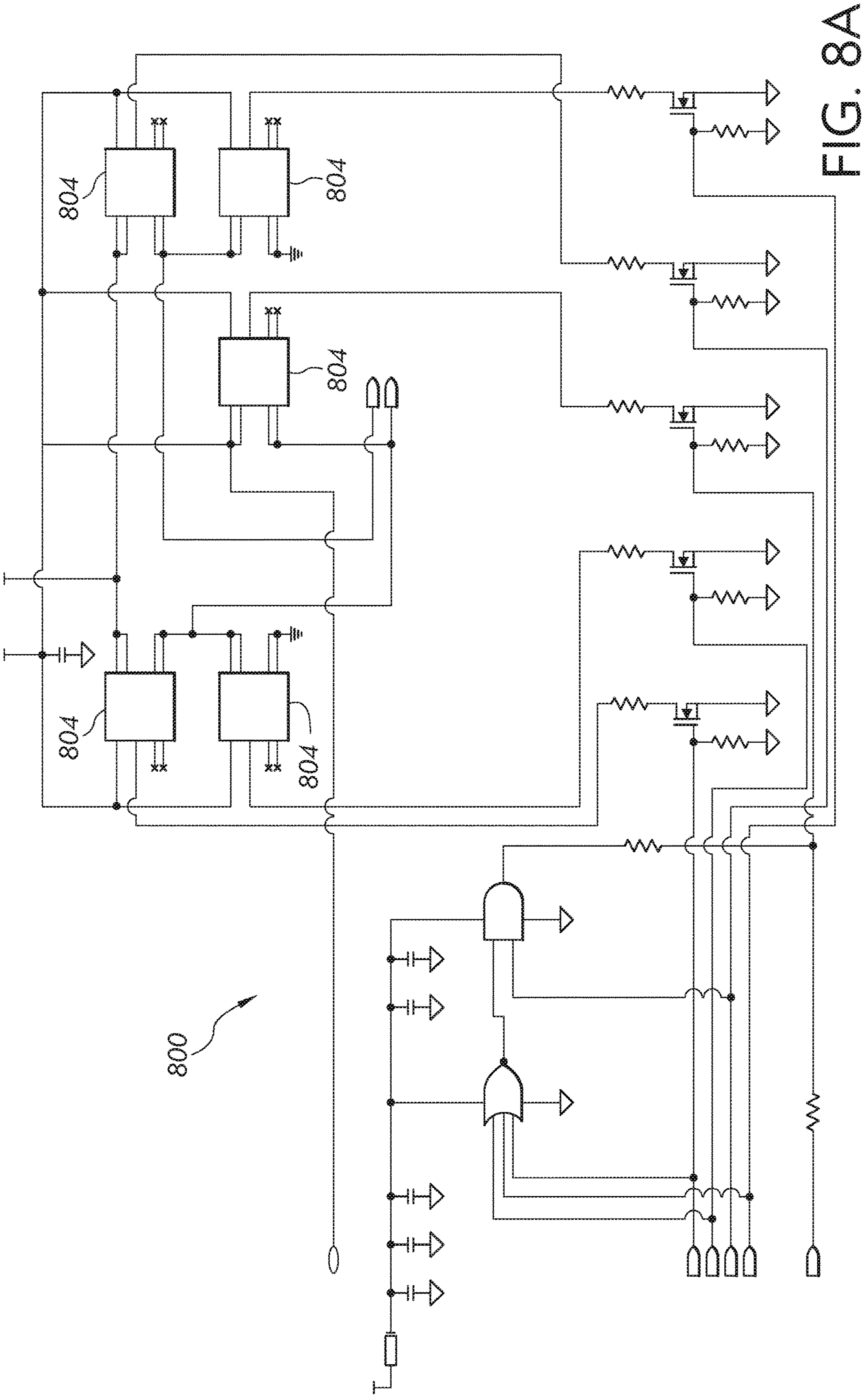
FIG. 8A schematically illustrates a power switch circuit configured to deliver different configurations of power to the two heating elements of the heated catheter through the hub, according to one or more embodiments shown and described herein.
Figure 8B:
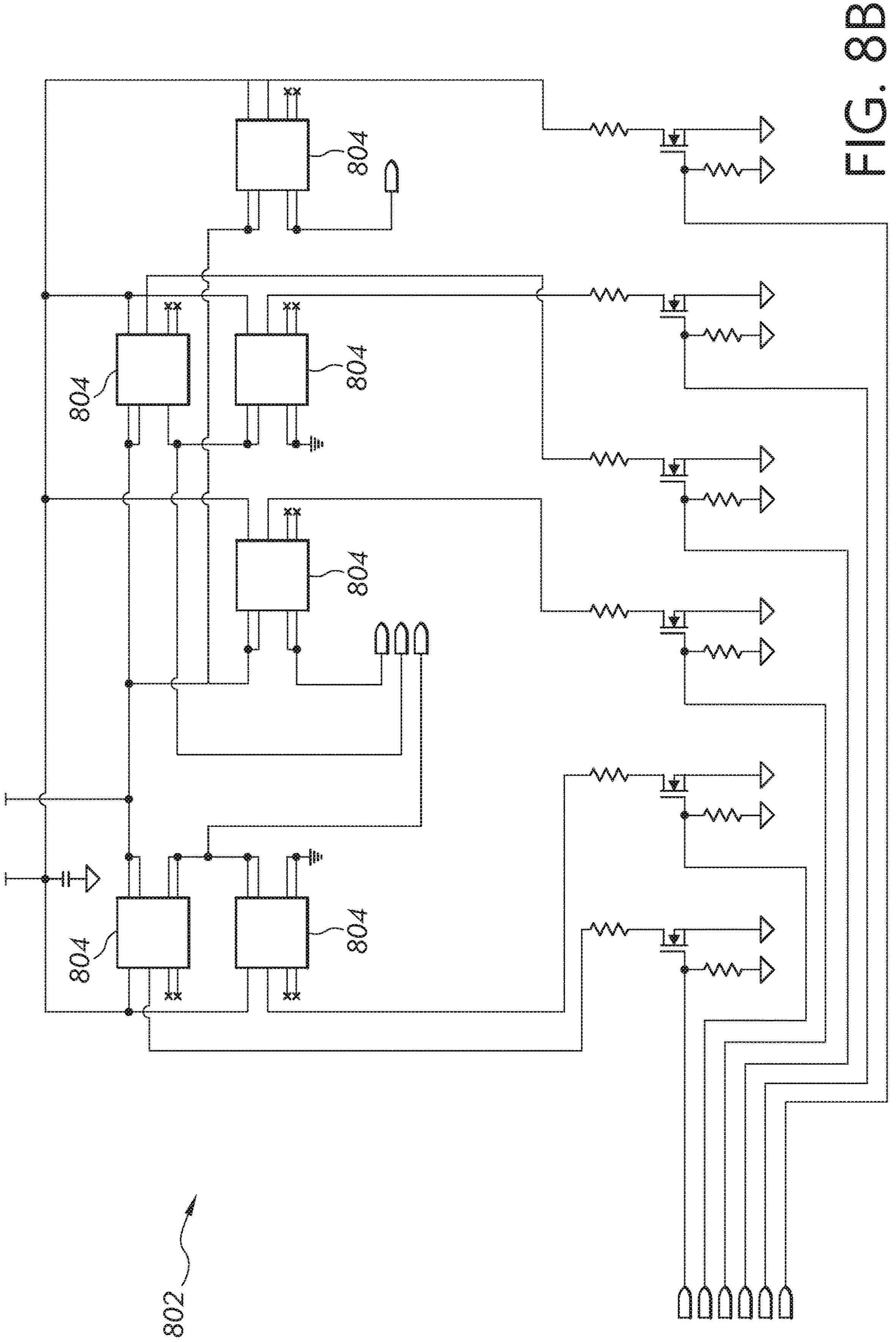
FIG. 8B schematically illustrates a power switch circuit configured to deliver different configurations of power to the three heating elements of the heated catheter through the hub, according to one or more embodiments shown and described herein.

FIG. 8A is a schematic of a circuit 800 to facilitate switching for a heated catheter 102 between a first heating length defined by the short heating element 402*a* and a second heating length defined by a combination of two heater segments comprising the short heating element 402*a* and the long heating element 402*b*. The circuit 800 of FIG. 8A is an example schematic for the power switch circuit 700 of FIG. 7. The H-bridge circuit configuration of the circuit 800 implements a truth table defining the combinations of signals driving either the legacy single-TRS connector catheters or the new dual-TRS connector catheters with their respective heating coil configurations. (e.g., see Table 2 above). This also facilitates backwards compatibility by providing a communication line to the heated catheter for the legacy single-TRS jack heater catheters. FIG. 8B is a schematic of a circuit 802 to facilitate switching for a heated catheter 102 switchable between a first heating length defined by the short heating element 402*a*, a second heating length defined by a combination of two heater segments comprising the short heating element 402*a* and the long heating element 402*b*, or a third heating length defined by a combination comprising the short heating element 402*a*, the long heating element 402*b*, and the extended heating element 402*c*. Additionally, the circuit 802 is configured to operate the heating catheters with one or two heating elements 402. In the illustrated examples, the circuits 800 and 802 includes power relays 804 to switch which of power, ground, and connection points of the heating elements 402.

The power switch circuits 700, 800, and 802 located in the energy delivery console 104 enables the dual-TRS connector 500 as described above and also facilitates the energy delivery console 104 maintaining backwards compatibility with catheters that use a legacy 6.35 mm single-TRS connector.

Figure 9:
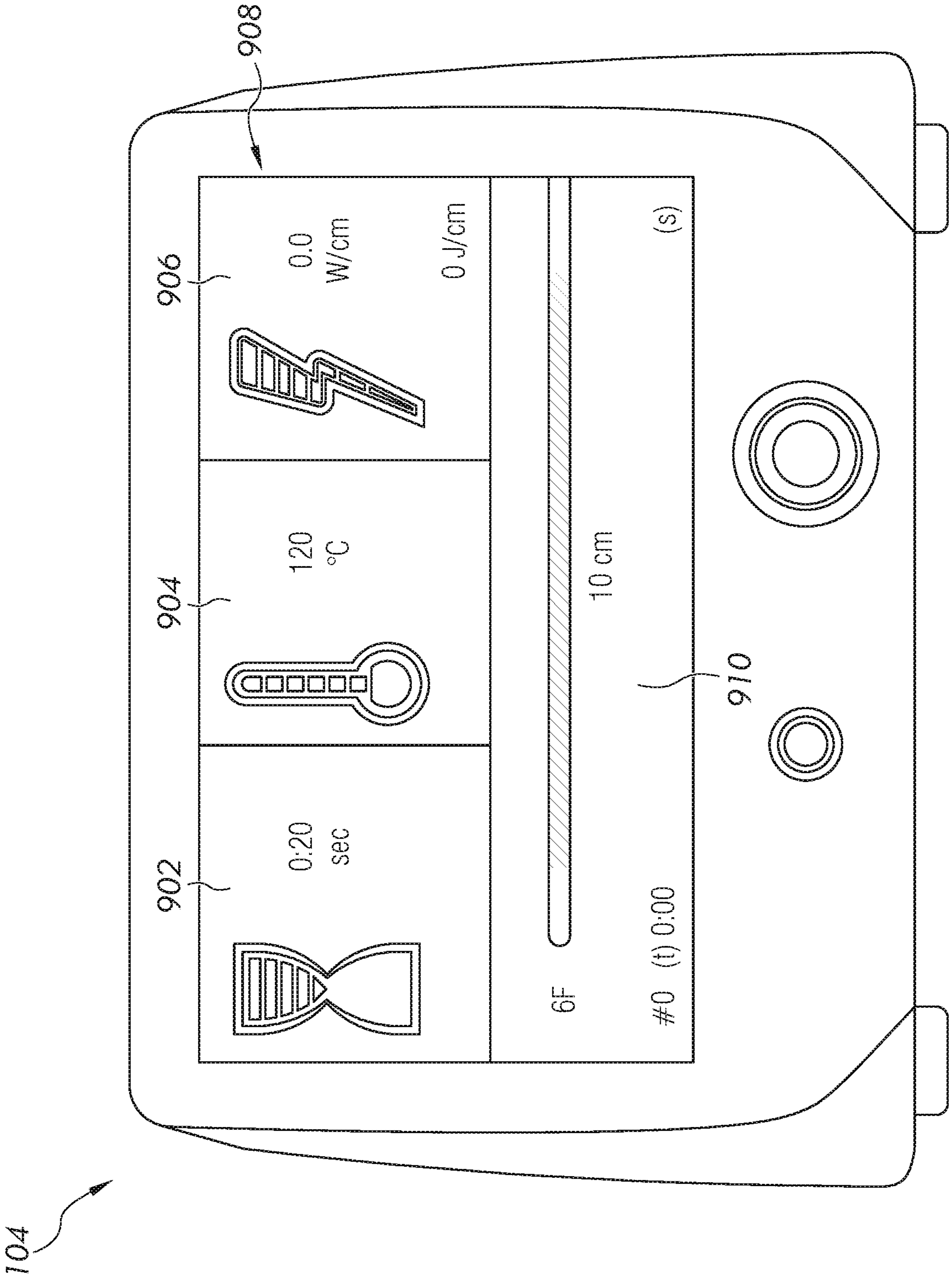
FIG. 9 depicts an example diagram of an example energy delivery console to deliver different configurations of power to the heated catheter, according to one or more embodiments shown and described herein.

FIG. 9 depicts an example diagram of an example energy delivery console 104. In a specific implementation, energy delivery console 104 can be located directly adjacent to the sterile field (such as placed on a pole stand with a boom arm to hold the unit nearly above the sterile field) or directly within the sterile field (such as if placed within a sterile envelope such as a see-through bag, or if the system and a power supply is configured to withstand sterilization such as by steam). Information can be provided to a user of energy delivery console 104 on display screen 900 (e.g., LCD, LED, flat-panel, touchscreen), by indicators (e.g., lights and/or sounds), or by interacting with a remote device such as a cell phone, tablet or computer. Exemplary information provided to a user may include power level 906 being delivered (e.g., instantaneous power in W or W/cm and/or cumulative power in Joules or J/cm), measured temperature 904 (e.g., ° C.), timer 902 (e.g., countdown or countup, seconds), alerts or status messages, identification information 908 of a connected heated catheter 102, history of earlier treatments, system and/or catheter settings, software revision of energy delivery system and copyright information. Multiple languages and date/time formats can be supported, as selectable by the user as well.

In a specific implementation, energy delivery console 104 can be powered by facility power (e.g., wall outlet in the range of 110-240 V AC), with a voltage regulator either built within the system or configured into the power cord (e.g., corded power supply system accepting 110-240 V AC as input and providing 24 V DC as output). Additionally, energy delivery console 104 can be battery-powered. Two or more power modules can be incorporated into the energy delivery console 104 in order to supply appropriate voltage for the microcontroller (e.g., 6-20 V, or 7 12V) and the energy delivery voltages (e.g., 12-24 V and 1-5 V, or 18-24 V and 1.8-3 V). In a specific implementation, the energy delivery console 104 is powered by facility power (e.g., 110-112 V or 220-240 V) and a microprocessor within heated catheter 102 is powered by a battery (e.g., 5 V). In a further implementation the battery inside heated catheter 102 has a pull-tab that interrupts power until it is pulled away by the user. In a further implementation the pull-tab is attached to heated catheter 102 packaging so that when the user removes heated catheter 102 from the packaging the pull-tab pulls away automatically.

Figure 10:
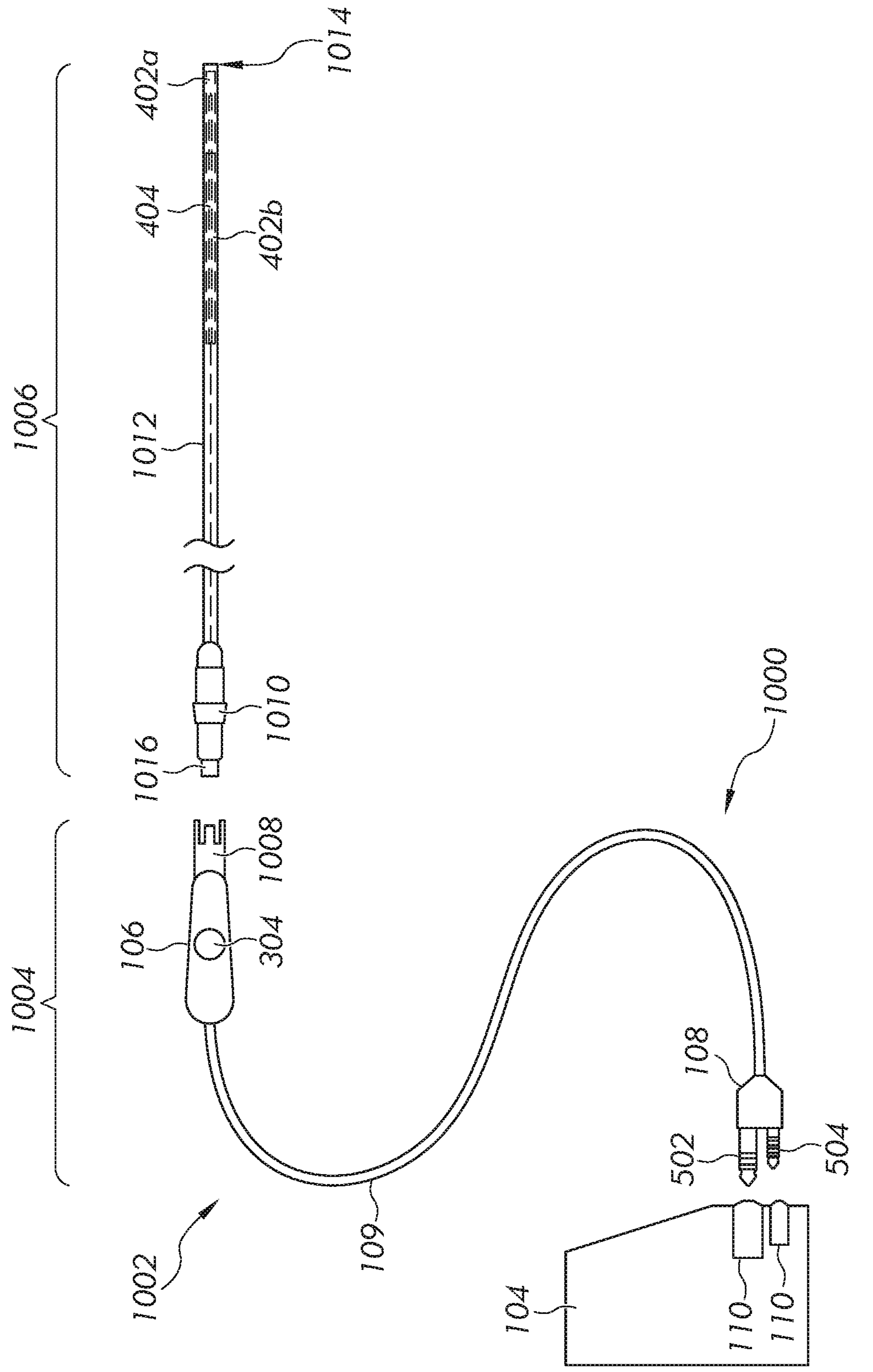
FIG. 10 schematically illustrates an example of an energy delivery system for providing endovenous thermal ablation with a detachable heated catheter, according to one or more embodiments shown and described herein

FIG. 10 illustrates an embodiment of depicts an energy delivery system 1000 for performing thermal ablation. In this example, the energy delivery system 1000 includes a heated catheter 1002, and the energy delivery console 104. The heated catheter 1002 may be a partially detachable version of the heated catheter 102. In the illustrated example, the heated catheter 1002 includes a hub portion 1004 and a head portion 1006. The detachability of the head portion 1006 facilitates the head portion 1006 being disposable. When the hub portion 1004 and a head portion 1006 are electrically coupled, the heated catheter 1002 operates as the heated catheter 102 of FIG. 1 described above. The hub portion 1004 includes the hub 106, the connector 108, and the wire harness 109 that electrically couples the hub 106 and the connector 108. The hub 106 includes a catheter connector 1008. The head portion 1006 includes a catheter head 1010 and a long, thin, flexible device 1012 that can be inserted into a narrow anatomical lumen such as a vein. In some examples, the catheter head 1010 also includes hub information component 302. The long, thin, flexible device 1012 includes the heating elements 402*a* and 402*b* and the temperature sensor 404 at its distal end 1014. The catheter head 1010 includes a catheter connector 1016. The hub 106 and the catheter head 1010 detachably coupled via the corresponding catheter connectors 1008 and 1016. The catheter connectors 1008 and 1016 may be mating connector halves, such as male and female halves of a high contact density push-pull or break-away circular connector with high current capacity. In some examples, the catheter connector 1008 of the hub 106 is the female connector and the catheter connector 1016 of the catheter head 1010 is the male connector.

These and other examples provided herein are intended to illustrate but not necessarily to limit the described implementation. As used herein, the term "implementation" means an implementation that serves to illustrate by way of example but not limitation. The techniques described in the preceding text and figures can be mixed and matched as circumstances demand to produce alternative implementations.

As used herein, the term "embodiment" means an embodiment that serves to illustrate by way of example but not limitation. The techniques described in the preceding text and figures can be mixed and matched as circumstances demand to produce alternative embodiments.

The following clauses provide further disclosure of the subject matter.

An energy delivery system, comprising: an energy delivery console; a catheter assembly configured to connect to and receive energy from the energy delivery console, the catheter assembly comprising first, second, and third heating elements being serially connected with a first number of connections to supply the energy to different configurations of the first, second, and third heating elements; and a hub disposed within or attached to the catheter assembly, the hub including a pair of polarity reversing diodes configured to drive the first, second, and third heating elements of the catheter assembly with a second number of connections disposed between the energy delivery console and the catheter cable assembly, the second number of connections being one less than the first number of connections.

The hub may further comprise a tip, ring, and sleeve (TRS) connector jack configured to electrically couple the second number of connections to a corresponding TRS connector plug of the energy delivery console.

The energy delivery console may further comprise a switching circuity to select between the different configurations of the first, second, and third heating elements based on switching different electrical states to the second number of connections.

The hub may further comprise: a memory chip configured to store operation data of the catheter assembly to facilitate energy delivery console identifying a configuration of the second number of connections; and a treatment cycle switch to provide a switchable signal to the energy delivery console.

The hub may further comprise: a first TRS connector jack having a first physical configuration configured to electrically couple the second number of connections to a corresponding first TRS connector plug of the energy delivery console; and a second TRS connector jack having a second physical configuration configured to electrically couple the memory chip and the treatment cycle switch to a corresponding second TRS connector plug of the energy delivery console, the second physical configuration different than the first physical configuration.

The energy delivery console may further comprise a switching circuity to select between the different configurations of the first, second, and third heating elements based on switching which electrical connections are coupled to the second number of connections.

The hub and the catheter assembly may include corresponding connectors to detachably connect to each other.

A hub to interface between a catheter assembly and an energy delivery console, the hub comprising: a tip, ring, and sleeve (TRS) connector jack configured to provide a first number of electrical connections to a corresponding TRS connector plug of the energy delivery console; and a pair of polarity reversing diodes connected to one of the first number of electrical connections, the hub configured to drive first, second, and third heating elements of the catheter assembly with a second number of connections, the second number of connections being one more than the first number of connections.

The hub may further comprise: a memory chip configured to store operation data of the catheter assembly to facilitate energy delivery console identifying a configuration of the second number of connections; and a treatment cycle switch to provide a switchable signal to the energy delivery console.

The TRS connector jack may be a first TRS connector jack, and the hub may further comprise a second TRS connector jack configured to electrically couple the memory chip and the treatment cycle switch to a corresponding second TRS connector plug of the energy delivery console, the first and second TRS connector jacks configured to inhibit incorrect insertion into the energy delivery console.

The energy delivery console may be configured to select between the different configurations of the first, second, and third heating elements by switching different electrical states to the first number of connections.

The first TRS connector jack may be a 6.3 mm TRS connector jack.

The second TRS connector jack may be a 3.5 mm TRS connector jack.

A connector assembly configured to electrically couple a heating catheter having a short heating element and a long heating element to an energy delivery console, the connector assembly comprising: a first connector jack configured to provide a first input electrical connection and a second input electrical connection to provide power for the heating catheter; a pair of polarity reversing diodes electrically coupled to the first input electrical connection, the pair of polarity reversing diodes electrically coupling the first input electrical connection to a first heating element connection and a second heating element connection, the second input electrical connection being electrically coupled to a third heating element connection; and a second connector jack configured to pass through communication signals between the heating catheter and the energy delivery console.

The first and second connector jacks may be configured to inhibit incorrect insertion into the energy delivery console.

The first connector jack may be a 6.3 mm tip, ring, and sleeve (TRS) connector jack, and the second connector jack may be a 3.5 mm TRS connector jack.

The connector assembly and the heating catheter may include corresponding connectors to detachably connect to each other.

The invention claimed is:

1. An energy delivery system, comprising:

an energy delivery console;

a heated catheter configured to connect to and receive energy from the energy delivery console, the heated catheter comprising a first heating element, a second heating element, and a third heating element being serially connected with a first number of connections to supply the energy to different configurations of the first heating element, the second heating element, and the third heating element; and a hub disposed within or attached to the heated catheter, the hub including a pair of polarity reversing diodes configured to drive the first heating element, the second heating element, and the third heating element of the heated catheter with a second number of connections disposed between the energy delivery console and the heated catheter, the second number of connections being one less than the first number of connections;

wherein the pair of polarity reversing diodes connects two heating coil-side terminals to one connector-side terminal.

2. The system of claim 1, wherein the hub further comprises a tip, ring, and sleeve (TRS) connector jack configured to electrically couple the second number of connections to a corresponding TRS connector plug of the energy delivery console.

3. The system of claim 2, wherein the energy delivery console further comprises a switching circuitry to select between the different configurations of the first heating element, the second heating element, and the third heating element based on switching different electrical states to the second number of connections.

4. The system of claim 1, wherein the hub further comprises:

a memory integrated circuit configured to store operation data of the heated catheter to facilitate energy delivery console identifying a configuration of the second number of connections; and a thermocouple reference switch to provide a switchable signal to the energy delivery console.

5. The system of claim 4, wherein the hub further comprises:

a first TRS connector jack having a first physical configuration configured to electrically couple the second number of connections to a corresponding first TRS connector plug of the energy delivery console; and a second TRS connector jack having a second physical configuration configured to electrically couple the memory integrated circuit and the thermocouple reference switch to a corresponding second TRS connector plug of the energy delivery console, the second physical configuration different than the first physical configuration.

6. The system of claim 5, wherein the energy delivery console further comprises a switching circuitry to select between the different configurations of the first heating element, the second heating element, and the third heating element based on switching which electrical connections are coupled to the second number of connections.

7. The system of claim 1, wherein the hub and the heated catheter include corresponding connectors to detachably connect to each other.

8. A hub to interface between a heated catheter and an energy delivery console, the hub comprising:

a tip, ring, and sleeve (TRS) connector jack configured to provide a number of terminals to a corresponding TRS connector plug of the energy delivery console; and a pair of polarity reversing diodes connected to one of the terminals, the hub configured to drive a first heating element, a second heating element, and a third heating element of the heated catheter with a number of connection points, the number of connection points being one more than the number of terminals;

wherein the pair of polarity reversing diodes connects two heating coil-side terminals to one connector-side terminal.

9. The hub of claim 8, further comprising:

a memory integrated circuit configured to store operation data identifying a configuration of the connection points; and a thermocouple reference switch to provide a switchable signal to the energy delivery console.

10. The hub of claim 9, wherein the TRS connector jack is a first TRS connector jack, and wherein the hub further comprises a second TRS connector jack configured to electrically couple the memory integrated circuit and the thermocouple reference switch to a corresponding second TRS connector plug of the energy delivery console, the first TRS connector jack and the second TRS connector jack configured to inhibit incorrect insertion into the energy delivery console.

11. The hub of claim 10, wherein the second TRS connector jack is a 3.5 mm TRS connector jack.

12. The hub of claim 9, wherein the energy delivery console is configured to select between the different configurations of the first heating element, the second heating element, and the third heating element by switching different electrical states to the terminals.

13. The hub of claim 9, wherein the first TRS connector jack is a 6.3 mm TRS connector jack.

14. A connector assembly configured to electrically couple a heating catheter having a short heating element and a long heating element to an energy delivery console, the connector assembly comprising:

a first connector jack configured to provide a first input electrical connection and a second input electrical connection to provide power for the heating catheter;

a pair of polarity reversing diodes electrically coupled to the first input electrical connection, the pair of polarity reversing diodes electrically coupling the first input electrical connection to a first heating element connection and a second heating element connection, the second input electrical connection being electrically coupled to a third heating element connection; and a second connector jack configured to pass through communication signals between the heating catheter and the energy delivery console;

wherein the pair of polarity reversing diodes connects two heating coil-side terminals to one connector-side terminal.

15. The connector assembly of claim 14, wherein the first TRS connector jack and the second TRS connector jack are configured to inhibit incorrect insertion into the energy delivery console.

16. The connector assembly of claim 15, wherein the first connector jack is a 6.3 mm tip, ring, and sleeve (TRS) connector jack, and the second connector jack is a 3.5 mm TRS connector jack.

17. The connector assembly of claim 15, wherein the connector assembly and the heating catheter include corresponding connectors to detachably connect to each other.

* * * * *